(12) United States Patent
Akaike

(10) Patent No.: US 7,182,338 B2
(45) Date of Patent: Feb. 27, 2007

(54) APPARATUS FOR DISCRIMINATING SHEET MATERIAL

(75) Inventor: Masatake Akaike, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 356 days.

(21) Appl. No.: 10/712,204

(22) Filed: Nov. 12, 2003

(65) Prior Publication Data

US 2004/0094458 A1  May 20, 2004

(30) Foreign Application Priority Data

Nov. 14, 2002 (JP) .............................. 2002-330273

(51) Int. Cl.
*B65H 7/02* (2006.01)
*G01L 1/22* (2006.01)
*G01L 1/04* (2006.01)

(52) U.S. Cl. ...................... 271/265.04; 73/862.474; 73/862.634; 73/862.639

(58) Field of Classification Search ........... 73/862.381, 73/862.471, 862.474, 862.634, 862.639; 250/559.01, 559.27, 559.39, 560, 561; 271/262, 271/263, 265.04; 400/56
See application file for complete search history.

(56) References Cited

U.S. PATENT DOCUMENTS

| | | | | |
|---|---|---|---|---|
| 3,171,034 A | * | 2/1965 | Walter et al. ........... 250/237 R |
| 3,822,588 A | * | 7/1974 | Knight et al. .................. 73/81 |
| 3,826,487 A | * | 7/1974 | Forster et al. .............. 271/263 |
| 4,060,734 A | * | 11/1977 | Tilley et al. ............ 250/559.27 |
| 4,141,253 A | * | 2/1979 | Whitehead, Jr. .............. 73/727 |
| 4,866,984 A | * | 9/1989 | Houghton ..................... 73/159 |
| 5,101,661 A | * | 4/1992 | Cresson et al. ............... 73/159 |
| 5,138,878 A | * | 8/1992 | Cresson et al. ............... 73/159 |
| 5,171,403 A | * | 12/1992 | Chase et al. ................. 162/197 |
| 5,188,983 A | * | 2/1993 | Guckel et al. ................ 438/53 |
| 5,486,063 A | * | 1/1996 | Fox et al. .................... 400/708 |
| 5,678,678 A | * | 10/1997 | Brandt et al. ............... 194/206 |
| 5,934,140 A | * | 8/1999 | Jackson et al. ............... 73/159 |
| 5,962,861 A | | 10/1999 | Fowler |
| 6,065,746 A | * | 5/2000 | Tranquilla ................... 271/176 |
| 6,365,895 B1 | * | 4/2002 | Yamamoto .................. 250/306 |
| 6,467,977 B2 | * | 10/2002 | Luque et al. ................. 400/56 |
| 6,485,205 B2 | * | 11/2002 | Luque .......................... 400/56 |
| 6,561,509 B2 | * | 5/2003 | Kettenmann et al. ....... 271/263 |
| 6,776,543 B1 | * | 8/2004 | Hall et al. ..................... 400/56 |
| 6,866,263 B2 | * | 3/2005 | Kawasaki ................... 271/262 |
| 7,043,962 B2 | * | 5/2006 | Sakai ........................ 73/12.01 |
| 2003/0053090 A1 | * | 3/2003 | Nojiri et al. ................. 358/1.9 |

\* cited by examiner

*Primary Examiner*—Patrick Mackey
*Assistant Examiner*—Matthew J. Kohner
(74) *Attorney, Agent, or Firm*—Morgan & Finnegan, LLP

(57) ABSTRACT

The present invention provides an apparatus for discriminating the kind of a sheet material, comprising: a substrate having a recessed portion; a press member situated so that a sheet material can be deflected using the recessed portion; a support member that is deformed as the sheet material situated to cover the recessed portion is pressed by the press member and thereby deflected; and a sensor for detecting the deformation amount of the support member, wherein the kind of the sheet material is discriminated on the basis of detecting the deformation amount of the support member by the sensor.

9 Claims, 11 Drawing Sheets

APPARATUS FOR DISCRIMINATING SHEET MATERIAL

BACKGROUND OF THE INVENTION

1. Field of the Invention

The present invention relates to an apparatus for discriminating the kind of a sheet material.

2. Related Background Art

Recently, sheet-material discriminating apparatuses for discriminating the kind of a sheet material have received attention in various technological fields. For example, it is desirable to automatically detect the kind of paper for use in printers, copiers and other image forming machines for keeping print quality at a satisfactory level. The apparatus for discriminating sheet material will be described below in this respect.

As shown in FIG. 11, a bar 106 is rotatably supported near a positioning roller 103 (U.S. Pat. No. 5,962,861). A force F acts on an end 105 of the bar 106 in a direction shown by the arrow. Now, the bar 106 slightly rotates in a clockwise direction (see symbol E) as a printing paper P is fed, but a displacement thereof varies depending on the material of the printing paper. Thus, the kind of the printing paper P can be discriminates by detecting the displacement with a sensor 108.

In the conventional apparatus described above, the printing paper P should be deflected under only the influence of the lifting force F from the bar 106. However, the printing paper P may be deflected under the influence of wind pressure if the speed at which the printing paper P is fed is high, and the printing paper P may be deflected simply by its own weight if it is thin. Thus, in such a case, it is difficult to discriminate the kind of a paper correctly. In addition, the printing paper P is susceptible to mechanical vibrations.

Thus, the present invention is to provide a new apparatus capable of correctly discriminating the kind of a sheet material. So far as discrimination of a sheet material is concerned, the apparatus and method according to the present invention may be applied without being specifically limited, and also they may be applied even if the speed at which the sheet material is fed is high, and the sheet material is thin.

SUMMARY OF THE INVENTION

The present invention has been made in view of the situations described above, and provides an apparatus for discriminating the kind of a sheet material, comprising:

a substrate having a recessed portion;

a press member situated so as to have access to the recessed portion;

a support member that is deformed as a sheet material situated to cover the recessed portion is pressed by the press member and thereby deflected; and a sensor for detecting a deformation amount of the support member, wherein the kind of the sheet material is discriminated on the basis of detecting the deformation amount of the sheet material by the sensor.

DETAILED DESCRIPTION OF THE PREFERRED EMBODIMENTS

The embodiment of the present invention will be described below with reference to FIGS. 1 to 10.

Figure 1:
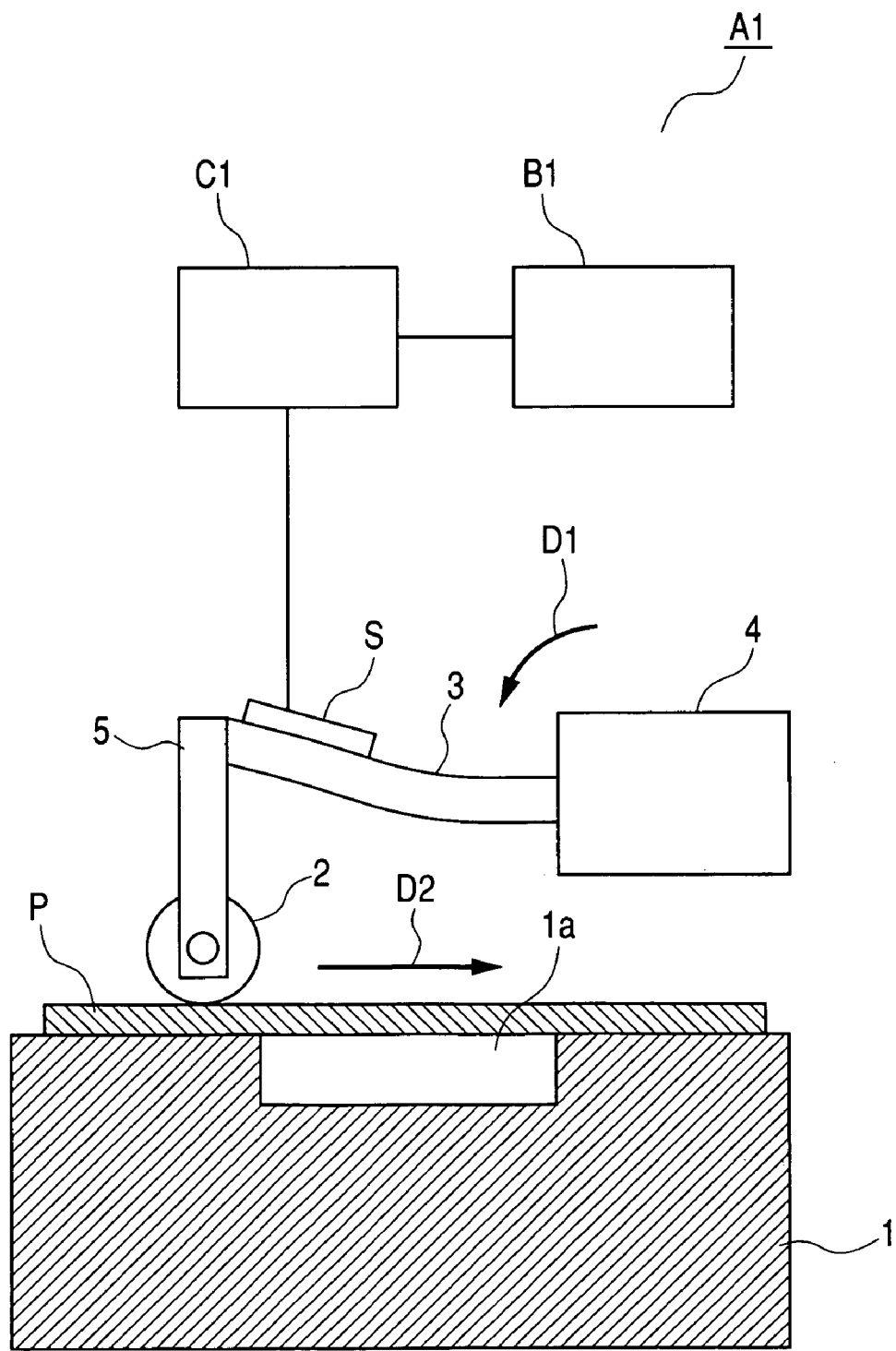
FIG. 1 is a schematic view showing one example of a structure (in which a roller 2 lies outside a groove 1a) of an apparatus for discriminating a sheet material according to the present invention.
Figure 2:
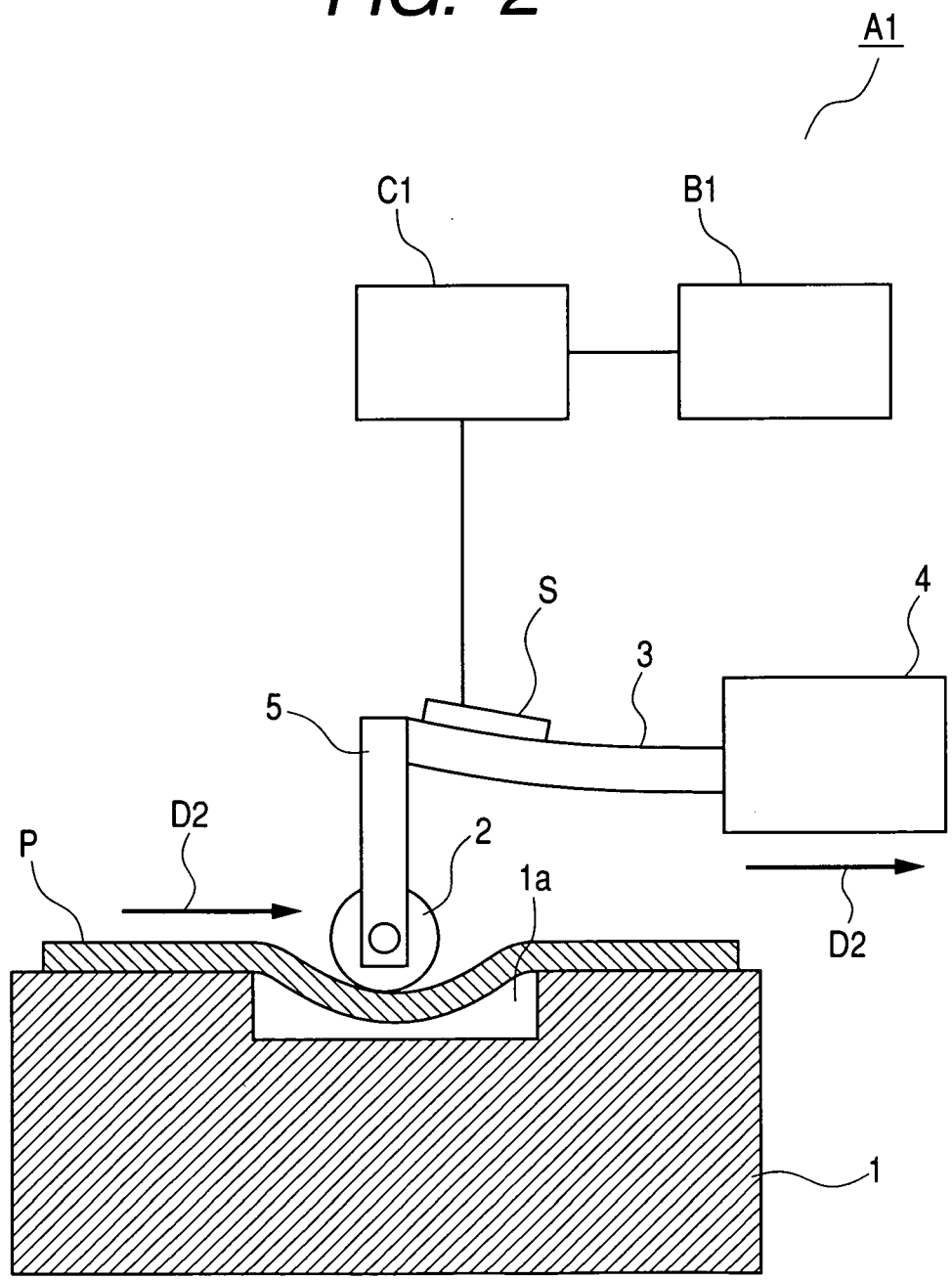
FIG. 2 is a schematic view showing one example of a structure (in which the roller 2 lies in the groove 1a) of the apparatus for discriminating a sheet material according to the present invention.
Figure 3:
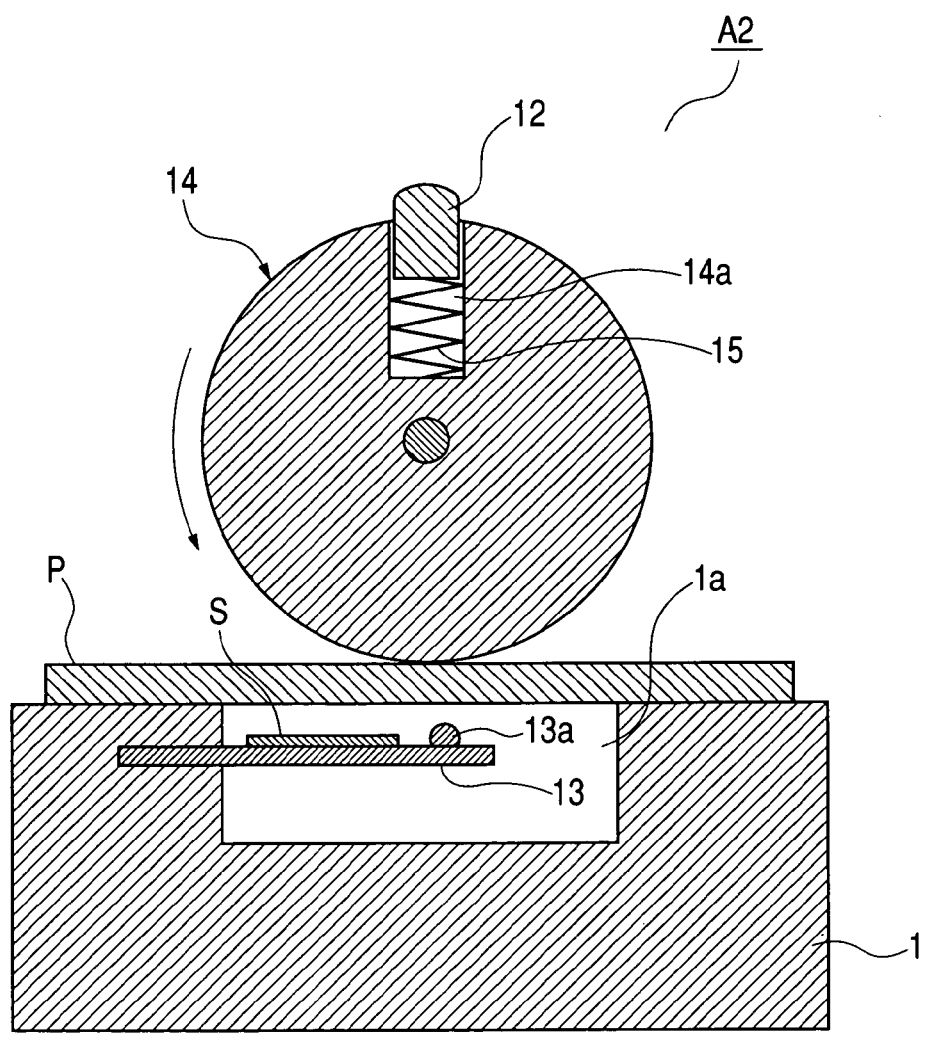
FIG. 3 is a schematic front view showing another example of a structure (in which a press member 12 lies outside the groove 1a) of the apparatus for discriminating a sheet material according to the present invention.

An apparatus for discriminating a sheet material according to this embodiment comprises a substrate 1 having a recessed portion 1a, and a press member 2 situated to have free access to the recessed portion 1a, as shown by symbol A1 in FIG. 1 and FIG. 2. When a sheet material P situated to cover the recessed portion 1a of the substrate 1 is pressed with a press member 2 (see FIG. 2), the sheet material P is pushed into the recessed portion 1a and thereby deflected, and an elastic support member 3 is deformed by an amount equivalent to the deflection amount, and the kind of the sheet material P can be discriminated on the basis of detecting the deformation amount of the elastic support member 3 by the deformation amount sensor S. Amounts detected with the deformation amount sensor S may include:

the deformation amount of the elastic support member 3 when the sheet material P is most deflected;

both the deformation amount of the elastic support member 3 when the sheet material P is not deflected and the deformation amount of the elastic support member 3 when the sheet material P is deflected; and the ratio of deformation of the elastic support member 3 in the process of deflection of the sheet material P (i.e. when the change of deformation amount of the elastic support member in the process of change in deflection amount of the sheet material is detected, and the kind of a sheet material is discriminated based on the change in deformation). Furthermore, if the deflection state can be varied depending on whether the sheet material is pressed with the press member or not, it is not required that the recessed portion on the substrate should be completely covered with the sheet material.

The apparatus for discriminating a sheet material according to the present invention has press member holding means 4 for holding the press member 2, and the press member holding means 4 should hold the press member 2 at a distance from the substrate 1 when the sheet material P is set in the substrate 1, and move the press member 2 to a position near the recessed portion 1a when the sheet material P is pressed.

Furthermore, as shown in FIGS. 3 to 6, the press member 12 held by press member holding means 14 may be moved by rotating press member holding means 14.

In addition, the press member holding means may hold the press member so that the press member contacts the sheet material P at a position other than the recessed portion.

Furthermore, as shown in FIG. 1, a first memory B1 for storing as data a relationship between the output signals of the deformation amount sensor S and the kind of the sheet material, and a first discrimination unit C1 for discriminating the kind of the sheet material P from the output signals of the deformation amount sensor S and data in the first memory B1 may be provided.

On the other hand, if "the deformation amount of the elastic support member 3 when the sheet material P is not deflected" and "the deformation amount of the elastic support member 3 when the sheet material P is deflected" are detected as described above, the press member holding means 4 described above may move the press member 2 along the sheet material P, and the sheet material P is not deflected when the press member 2 lies in a position other than the recessed portion (see FIG. 1); or the sheet material P is deflected when the press member 2 lies in a position near the recessed portion 1a (see FIG. 2). For this purpose, a second memory (not shown) for storing the deformation amount of the elastic support member 3 when the sheet material P is not deflected, and a deformation amount difference calculating means (not shown) for calculating a difference between "the deformation amount of the elastic support member 3 when the sheet material P is deflected" and "the deformation amount stored in the second memory" may be provided to discriminate the kind of the sheet material from the difference in deformation amounts. In this case, a third memory (not shown) storing a relationship between the difference in deformation amount and the kind of the sheet material, and a second discrimination unit (not shown) for discriminating the kind of sheet material from the result by the deformation amount difference calculating means and data in the third memory may be provided to discriminate the kind of sheet material by the second discrimination unit.

Furthermore, in the apparatus shown in FIGS. 1 and 2, the press member 2 is moved, but this embodiment is not limited thereto, and the substrate and the recessed portion may be moved with the press member 2 fixed at a certain position. FIGS. 7 to 10 show one example thereof, in which a roller 11 having a recessed portion 11a is rotated instead of moving press member 2.

When the change of deformation amount of the elastic support member is detected in the process of change in deflection amount of the sheet material, and the kind of the sheet material is discriminated based on the change in deformation amount, a fourth memory (not shown) for storing as data a relationship between the deformation amount of the elastic support member 3 and the kind of sheet material, and a third discrimination unit (not shown) for discriminating the kind of the sheet material from the detected change in deformation amount of the elastic support member 3 and data in the fourth memory may be provided.

In addition, press force imparting means for imparting a press force to the press member 2 may be provided. Such press force imparting means may include:

means such that the press member holding means 4 is tilted to apply a bending moment to the press member 2 as shown by symbol D1 in FIG. 1; and a load is applied directly to the press member 2 as shown by symbol W in FIGS. 7 to 10 instead of applying a bending moment. Furthermore, the load W may be a concentrated load or distributed load, and the load application point may be just above the press member 2 or at a different location.

The press member holding means 14 shown in FIGS. 3 to 6 rotatably supports the press member 12 so that the press member 12 comes close to or moves away from the recessed portion 1a, wherein the sheet material P is deflected when the press member 12 is close to the recessed portion 1a; and the sheet material P is not deflected when the press member 12 is at a distance from the recessed portion 1a. Even in the case of an apparatus having such a configuration, press force imparting means for imparting a press force to the press member 12 may be provided. The press force imparting means may include a spring member installed between the press member 12 and the press member holding means 14 (see symbol 15). A force F1 acting on the sheet material P from the press member 12 equals a sum of a force F2 acting on the press member 12 from the sheet material P and a force F3 acting on the press member 12 from an elastic support member 13 (i.e. F1=F2+F3). Here, provided that the magnitude of F1 is constant irrespective of the kind of the sheet material, the magnitudes of F2 and F3 depend on the material quality of the sheet material P such that the reaction force F2 increases while the force F3 decreases for a sheet material of high rigidity, and the reaction force F2 decreases while the force F3 increases for a sheet material of low rigidity. When the deformation amount of the elastic support member 13 is detected with the sensor S, the magnitude of F3 can be known and as a result, the material quality of the sheet material P can be discriminated.

In the apparatus shown in FIGS. 1 and 2, the elastic support member 3 and the press member 2 are coupled together and placed outside the recessed portion 1a, and the elastic support member 3 is deformed when the press member 2 presses the sheet material P, but this embodiment is not limited to such a structure. For example, a structure is also acceptable in which the press member is placed outside the recessed portion 1a as shown by symbol 12 in FIGS. 3 to 6, the elastic support member is placed inside the recessed portion 1a as shown by symbol 13 in these figures, and the elastic support member 13 is deformed on the basis of pressing it via the sheet material P by the press member 12.

In addition, elastic support members 3 and 13 in these figures are cantilever beams (flat springs) supported horizontally, but as long as they are elastically deformed, they may have shapes other than the plane shape, may be twin beams instead of cantilever beams, or may be supported vertically instead of being supported horizontally. Furthermore, if elastic support members 3 and 13 are flat springs, they may be made of stainless steel, carbon steel, Si—Mn steel, Cr—V steel, brass, beryllium copper and the like.

Here, the deformation amount sensor S may be a piezoelectric member, specifically a piezoelectric member made of lead zirconate titanate (PZT), barium titanate or zinc oxide.

It is sufficient that the recessed portion in the present invention can sustain deflection of a certain area of the sheet material P occurring when the press force is applied. Thus, the recessed portion conceptionally includes not only the substrate surface having only a certain area recessed (recessed area such as groove) as shown by symbols 1a and 11a in FIGS. 1 and 10, but also a portion cutting through the substrate from the front side to the back side such as a hole or opening.

Figure 7:
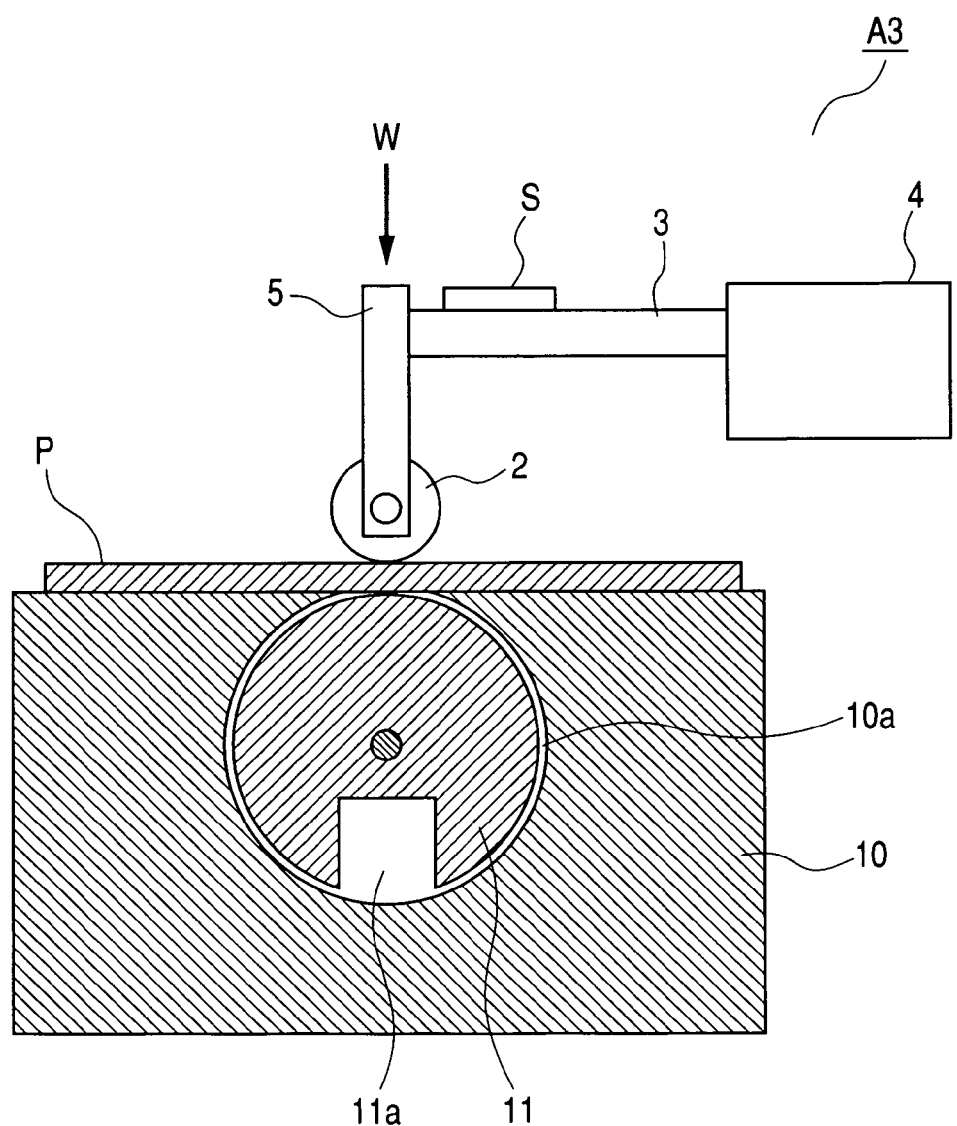
FIG. 7 is a schematic front view showing still another example of a structure (in which the roller 2 lies outside an recessed portion 11a) of the apparatus for discriminating a sheet material according to the present invention.
Figure 8:
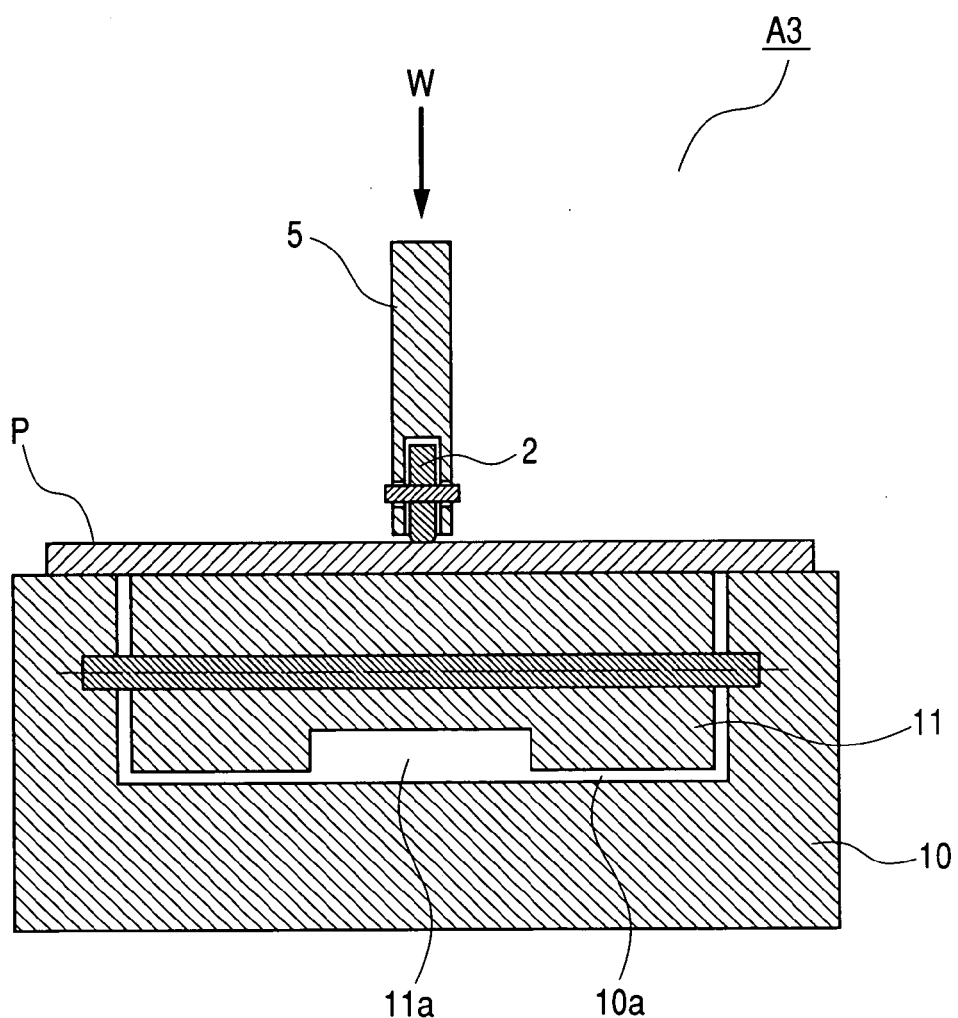
FIG. 8 is a schematic side view showing still another example of a structure (in which the roller 2 lies outside the recessed portion 11a) of the apparatus for discriminating a sheet material according to the present invention.
Figure 9:
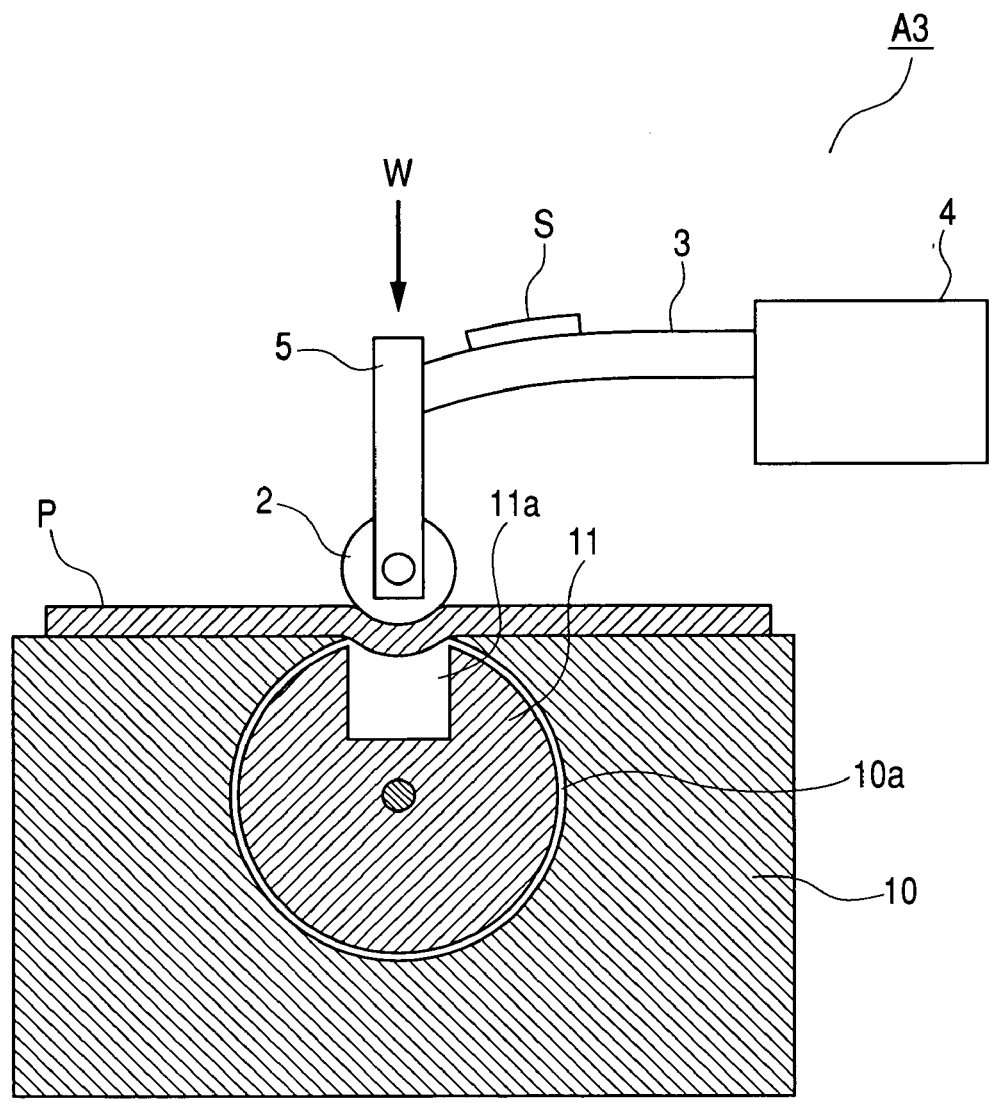
FIG. 9 is a schematic front view showing still another example of a structure (in which the roller 2 lies in the recessed portion 11a) of the apparatus for discriminating a sheet material according to the present invention.
Figure 10:
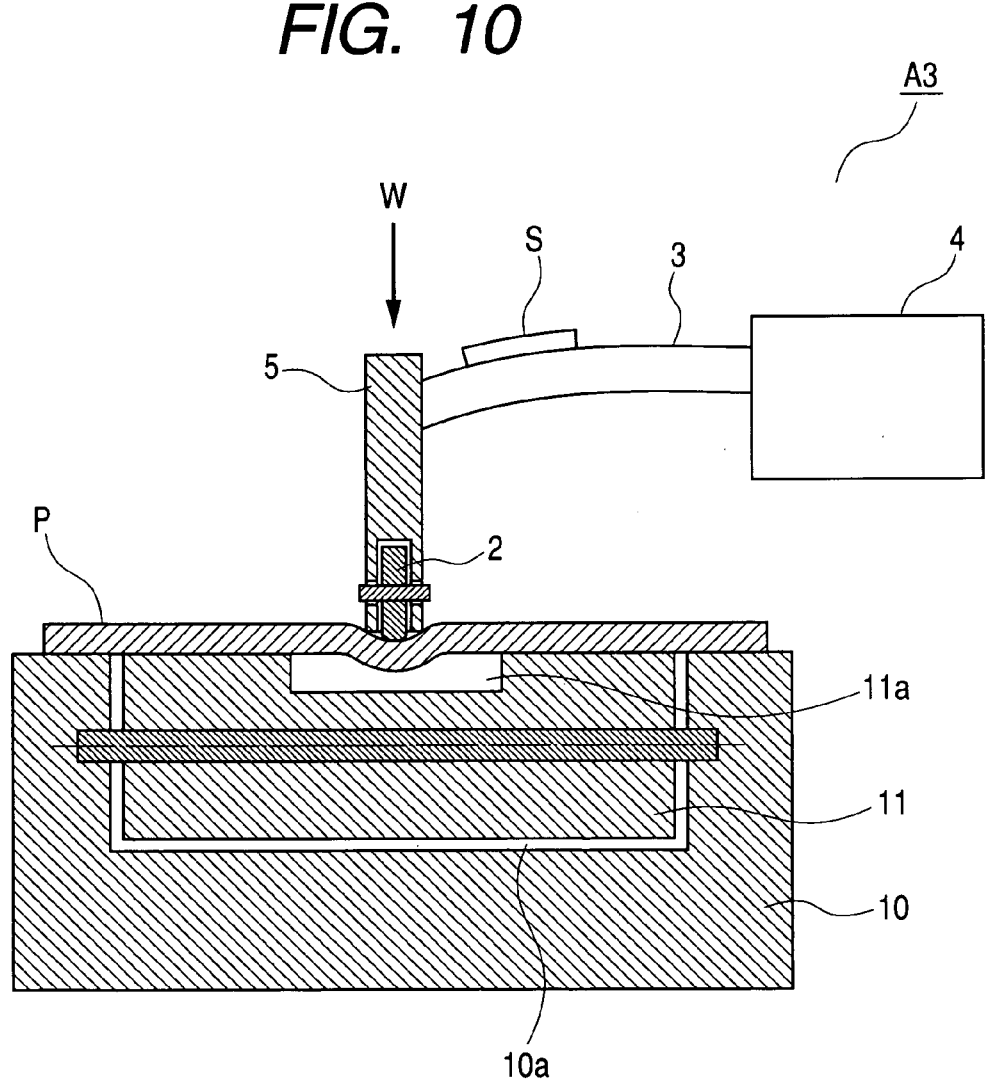
FIG. 10 is a schematic side view showing still another example of a structure (in which the roller 2 lies in the recessed portion 11a) of the apparatus for discriminating a sheet material according to the present invention.
Figure 11:
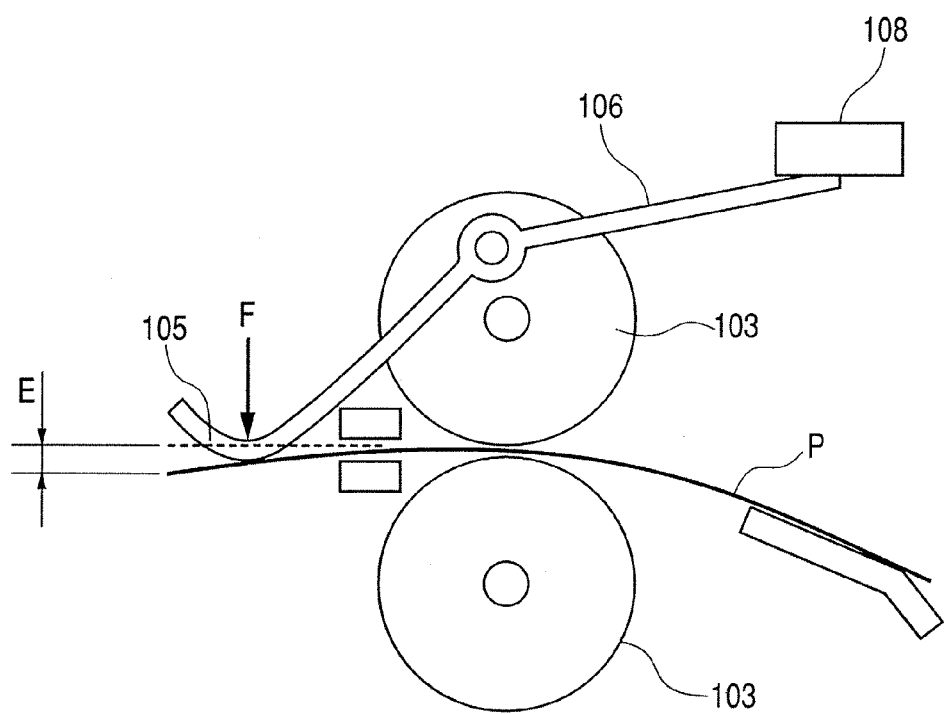
FIG. 11 is a schematic view showing one example of a conventional structure.

In addition, the substrate in the present invention is not limited as long as it holds a part of sheet material P when the press force is applied, and conceptionally includes a plane plate-like platen (e.g. platen of image forming apparatus) as shown by symbol in FIGS. 1 to 6, a rotating roller (e.g. paper feed roller) as shown by symbol 11 in FIGS. 7 and 10, and other forms. That is, the substrate may be only capable of holding the sheet material P and sustaining the deflection of a certain area of the sheet material, and therefore it may be a ring, cylinder, rod or the like in shape.

Furthermore, the sheet material P may be a printing paper or the like.

The press member 2 shown in FIG. 1 and the like is a roller rotatably supported by a rotating shaft, but may have a form other than the roller. For press members 2 and 12, materials having large Young's modulus and hardness and specifically, they may be made of any of iron, nickel, chromium, tungsten, molybdenum, alloys thereof, oxides of these metals, aluminum oxides, silicon oxides, silicon nitrates, zircon oxides, ceramics thereof, glass and polymer materials.

The sheet-material discriminating apparatuses having various configurations described above may be provided in image forming apparatuses such as copiers and printers to detect the kind of a sheet material (i.e. printing paper).

A method for discriminating a sheet material according to the present invention will now be described.

The method for discriminating a sheet material according to the present invention comprises:
  a step of deflecting a predetermined area of a sheet material by applying a press force F1 thereto;
  a step of placing an elastic support member so that the elastic support member is deformed by an amount corresponding to a deflection amount of the sheet material;
  a step of detecting a deformation amount of the elastic support member; and
  a step of discriminating the kind of a sheet material based on the results of the detection.

Advantages of this embodiment will now be described.

According to this embodiment, the kind of a sheet material P is discriminated while the sheet material P is supported by a substrate 1. Thus, the sheet material P is hard to be deflected by its weight even when it is thin (or it has a low bending rigidity), the sheet material is hard to be displaced under influences of wind and mechanical vibrations, and the amount of deflection of the sheet material P by press members 2 and 12 can be accurately detected to correctly discriminate the kind of the sheet material P.

In addition, according to this embodiment, the sheet material P is hard to be displaced under influences of wind and mechanical vibrations, thus making it possible to correctly discriminate the kind of sheet material P in the process of feeding of the sheet material P.

Furthermore, when a piezoelectric member is used as a deformation amount sensor S, no power source is required for detecting a signal of deformation, thereby resulting in a simplified structure.

Furthermore, the above recessed portion preferably has a depth sufficient to prevent the sheet material from contacting the bottom of the recessed portion even when the sheet material is pressed with the press member.

The present invention will be described further in detail below based on Examples.

EXAMPLE 1

In this Example, an apparatus A1 shown in FIGS. 1 and 2 was fabricated.

FIGS. 1 and 2 well represent the feature of the present invention and in these figures, reference numeral 1 denotes a platen on which a printing paper (sheet material) P is placed, and reference symbol 1a denotes a groove (recessed portion) formed in the platen 1. In addition, reference numeral 3 denotes a flat spring (elastic support member), reference symbol S denotes a piezoelectric member (deformation amount sensor) provided on the surface of the flat spring 3, reference numeral 5 denotes a press shaft integrated with the flat spring 3, reference numeral 2 is a roller (press member) for pressing the printing paper P, and reference numeral 4 denotes a movable fixed end (press member holding means) for supporting the flat spring 3 and the roller 2 and moving them along the printing paper P.

Then, in the configuration described above, the printing paper P is placed on the platen 1, the roller 2 is placed above the printing paper P and at a position other than the groove 1a and thereafter, the movable fixed end 4 is rotated in the direction of arrow D1 as shown in FIG. 1. Consequently, the roller 2 contacts the printing paper P, and thus the flat spring 3 is deflected. As the movable fixed end 4 is moved in the direction of arrow D2, the roller 2 causes the printing paper P to be deflected towards the groove 1a as shown in FIG. 2. Furthermore, when the movable fixed end 4 is rotated in the direction of arrow D1 (i.e. the roller 2 contacts the printing paper P), a bending moment occurs in the flat spring 3, and the bending moment changes in the following manner as the roller 2 moves in the direction of arrow D2. Specifically, the bending moment
  is kept constant when the roller 2 lies in a position other than the groove 1a, but
  gradually decreases when the roller 2 enters the groove 1a,
  decreases to a minimum when the roller 2 reaches almost the center of the groove a1 (a position at which deflection of its printing paper P reaches a maximum) (see FIG. 2),
  gradually increases as the roller 2 moves from the center of the groove 1a to the periphery, and
  becomes constant when the roller 2 leaves the groove 1a.

Furthermore, the deformation amount of the flat spring 3 changes in proportion to the magnitude of the bending moment, and the deformation amount is detected with the piezoelectric member S (in the strict sense, the piezoelectric member S is deformed, and the deformation amount thereof is detected as a voltage value). The output voltage of the piezoelectric member S varies depending on the kind of the printing paper P (bending rigidity in the strict sense) (specifically, the output voltage decreases when the bending rigidity increases, and the output voltage increases when the bending rigidity decreases), and the kind of printing paper P can be discriminated from the output voltage.

Ordinary paper (CP 250 manufactured by Canon Inc.), coat paper (HR 101s manufactured by Canon Inc.) and glossy paper (PR 101 manufactured by Canon Inc.) were set one after another to determine the output voltage of the piezoelectric member S and as a result, it was found that the output voltage of the ordinary paper was the highest value, and the output voltages of the coat paper and the glossy paper decreased in mentioned order.

According to this Example, the kind of a printing paper P is discriminated in a state that the printing paper P placed on the platen 1, and therefore the kind can be correctly discriminated even when the printing paper P is thin, and wind and mechanical vibrations occur.

Furthermore, the discrimination of a paper in this Example is performed using the output voltage of the piezoelectric member S when the printing paper is most deflected, but the discrimination of a paper may be performed using a difference between the output voltage when the printing paper is not deflected and the output voltage when the printing paper is most deflected, or using a rate of change in output voltage in the process of deflection of the printing paper.

EXAMPLE 2

In this Example, an apparatus A3 shown in FIGS. 7 to 10 was fabricated. Furthermore, the same parts as those of Example 1 are given the same symbols, and overlapped descriptions thereof are omitted here.

FIGS. 7 to 10 well represent the feature of the present invention and in these figures, reference numeral 10 denotes a platen on which a printing paper P is placed, reference symbol 10a denotes a cylindrical hollow portion formed on the platen 10, reference numeral 11 denotes a lower roller (corresponding to the "substrate" described in claims) installed in the hollow portion 10a, and reference symbol 11a denotes a recessed portion formed in the lower roller 11. In addition, reference numeral 4 denotes a movable fixed end (press member holding means) supporting a flat spring 3 and an upper roller 2 and moving them along the printing paper P. Furthermore, this movable fixed end 4 cannot be rotated unlike the movable fixed end of Example 1, but the upper roller 2 is pressed against the printing paper P by applying a concentrated load W along the axis of a press shaft 5.

Then, in the configuration described above, the printing paper P is placed on the platen 10 as shown in FIG. 7, and the upper roller 2 is placed on the printing paper P to apply the load W.

As the lower roller 11 is rotated in this state, the deflection amount of the flat spring 3 changes in the following manner. Specifically, the deflection amount of the flat spring 3 remains unchanged when the recessed portion 11a lies at a position other than the position of the upper roller 2, but gradually increases while the recessed portion 11a rotates and the upper roller 2 enters the recessed portion 11a, reaches the maximum at the time when the center of the recessed portion 11a matches the upper roller 2 (see FIGS. 9 and 10), gradually decreases as the recessed portion 11a further rotates, and becomes constant when the roller 2 leaves the recessed portion 11a.

Furthermore, the deformation amount of the flat spring 3 is detected with the piezoelectric member S, and by determining a change in strain amount per unit time ($d\epsilon/dt$), the kind of paper can be discriminated.

Ordinary paper (New Printer Paper; CP 250 manufactured by Canon Inc.), coat paper (Ultra Glossy Thick type; PR 101 manufactured by Canon Inc), OHP paper (Color BJ Transparency; CF 301 manufactured by Canon Inc) were set one after another to determine the strain amounts thereof. As a result, it was found that the strain amount of ordinary paper, glossy paper and OHP paper decreased in mentioned order, i.e. ordinary paper>glossy paper>OHP paper. Thus, in this Example, the same effect as that of Example 1 could be obtained.

Furthermore, the piezoelectric member S was bonded to the flat spring 3 with an adhesive, and no voltage was applied to the piezoelectric member S.

When this method is used, no input power source to the piezoelectric member S is required, and therefore electric circuitry for measurement is simplified, and power savings are achieved. Because the hollow portion 10a is provided in the platen 10 on which the printing paper P is placed, and the kind of paper is detected in the process of transference of the printing paper P over the hollow portion 10a from a paper feeding tray, the structure is simplified.

Furthermore, in this Example, the load W is a fixed load, and always presses the printing paper P, and when the upper roller 2 lies in the recessed portion 11a in association with rotation of the lower roller 11, the printing paper P is deflected and at the same time, the flat spring 3 is deformed in response to the deflection.

In this Example, the recessed portion 11a had a depth of 1 mm, a width of 3 mm and a length of 5 mm, the roller 11 had a diameter of 10 mm, and the load W was any fixed load in the range of 10 gf to 50 gf, which was provided by a coil spring (not shown). Beryllium copper was used as the flat spring 3, and lead zirconate titanate was used as the piezoelectric member S.

According to this Example, the structure is simplified, and power savings are achieved because no input power source for measuring sensors is required. In addition, because the kind of paper is detected during a dynamic period over which the printing paper P is transferred from the paper feeding tray to a print location, it is not necessary to temporarily stop the feeding of paper for detection of the kind of paper, thus making it possible to save time.

EXAMPLE 3

In this Example, an apparatus A2 shown in FIGS. 3 to 6 was fabricated. Furthermore, the same parts as those of Examples 1 and 2 are given the same symbols, and overlapped descriptions thereof are omitted here.

FIGS. 3, 4, 5 and 6 well represent the feature of the present invention, and a roller 14 for feeding a printing paper was placed above a recessed portion 1a of a platen 1. A hole portion 14a was provided in the roller 14, and a coil spring 15 and a press member 12 were placed in the hole portion 14a. That is, the roller 14 serves as press member holding means, and the coil spring 15 serves as press force imparting means for imparting a press force to the press member 12. In addition, a flat spring (elastic support member) 13 supported on one side and a piezoelectric member (deformation amount sensor) S bonded to the flat spring 13 were placed in the recessed portion 1a of the platen 1. Furthermore, reference symbol 13a denotes a raised portion situated at the leading end of the flat spring 13 and contacting the printing paper P.

Figure 4:
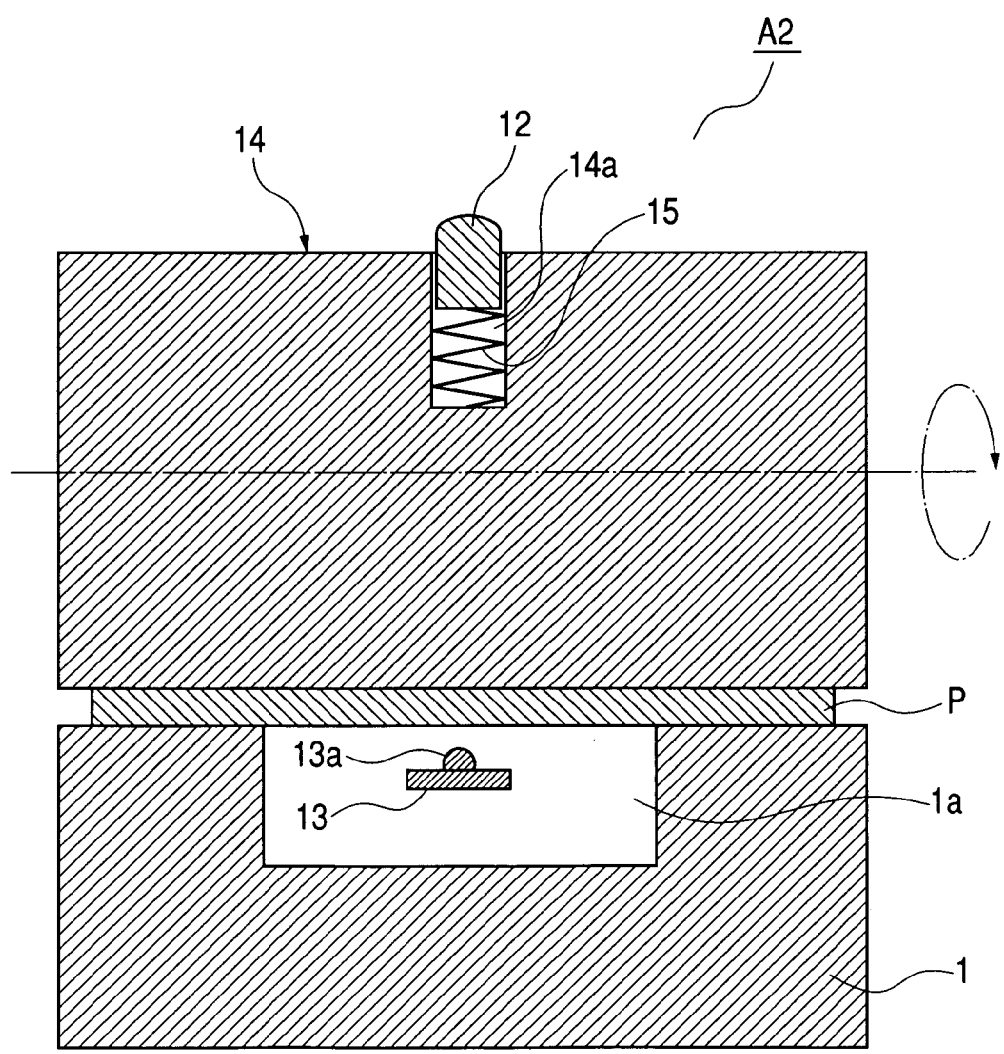
FIG. 4 is a schematic side view showing another example (in which the press member 12 lies outside the groove 1a) of the apparatus for discriminating a sheet material according to the present invention.
Figure 5:
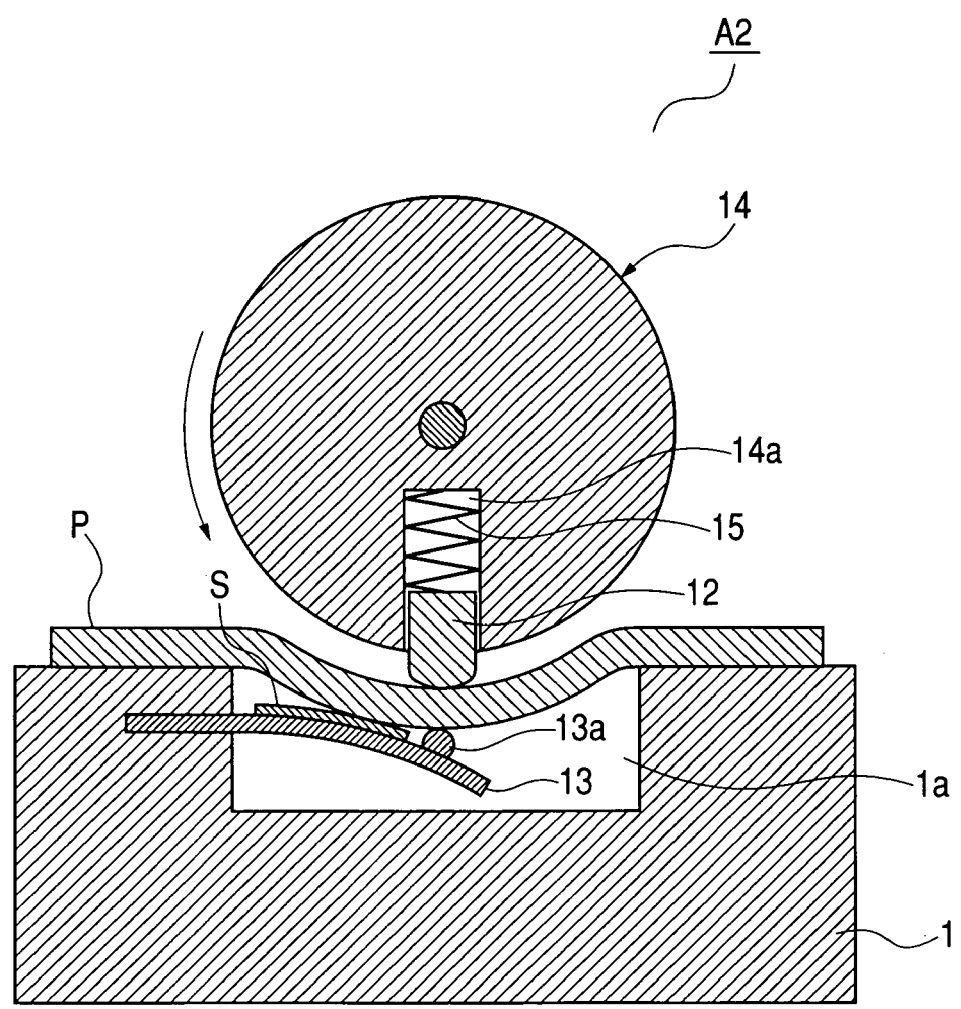
FIG. 5 is a schematic front view showing another example of a structure (in which the press member 12 lies in the groove 1a) of the apparatus for discriminating a sheet material according to the present invention.
Figure 6:
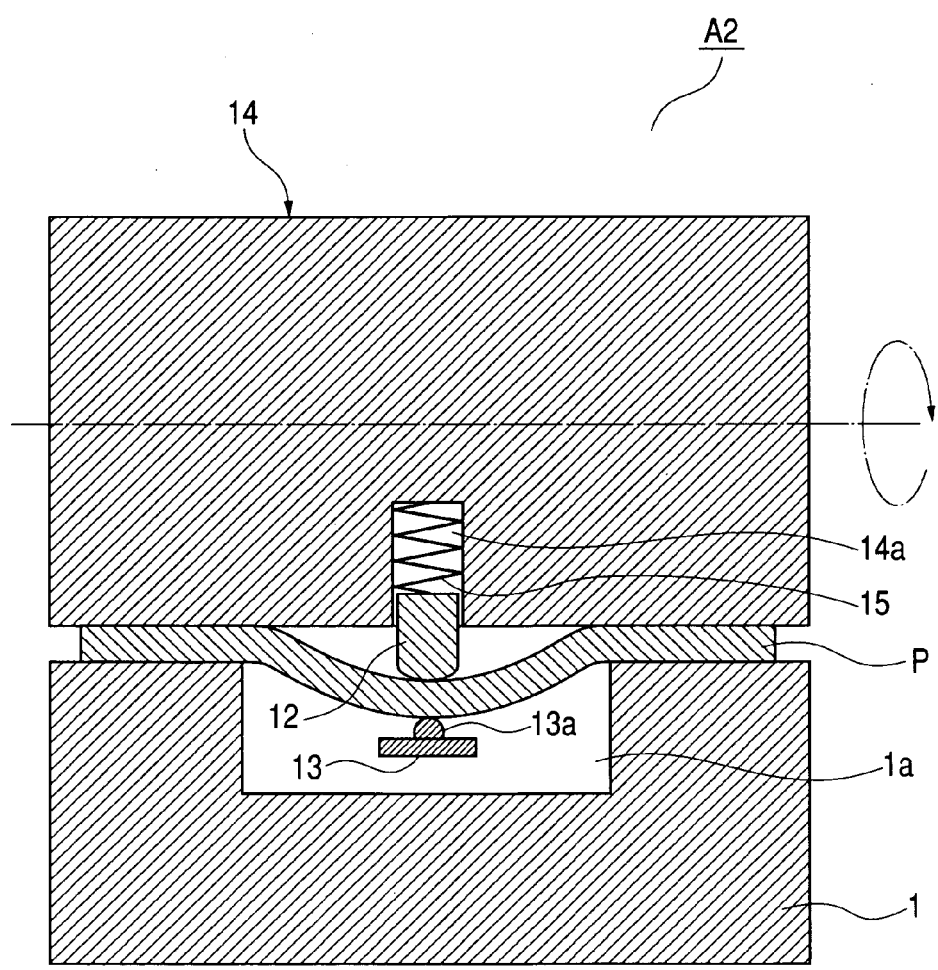
FIG. 6 is a side view showing another example of a structure (in which the press member 12 lies in the groove 1a) of the apparatus for discriminating a sheet material according to the present invention.

The apparatus A2 fabricated in this Example has a configuration such that the printing paper P is held between the platen 1 and the roller 14 because the roller 14 has an axial length greater than the size of the recessed portion 1a as shown in FIG. 4. Thus, when this roller 14 is rotated, the printing paper P is fed over the platen. Here, the printing paper P is never deflected in the recessed portion 1a as long as the press member 12 does not enter the recessed portion 1a, but the printing paper P is deflected inwardly in the recessed portion 1a when the roller 14 rotates to cause the press member 12 to enter the recessed portion 1a (see FIGS. 5 and 6), and the flat spring 13 is deformed. Furthermore, the deformation amount gradually increases as the roller 14 rotates, reaches a maximum in the state of FIG. 5, and then decreases. Accordingly, the strain amount of the piezoelectric member S changes, which is detected as a change in voltage.

In this Example, the recessed portion 1a had a depth of 2 mm, a width of 5 mm and a length of 20 mm, and the roller 14 had a diameter of 10 mm. In addition, the spring force of the coil spring 15 described above could be adjusted with a screw (not shown), and a press force from the press member 12 could be arbitrarily set within the range of 10 gf to 50 gf. Furthermore, the flat spring 13 and the raised portion 13a were adjusted so that the raised portion 13a always contacted the printing paper P.

Ordinary paper (New Printer Paper; CP 250 manufactured by Canon Inc.), glossy paper (Ultra Glossy Thick type; PR 101 manufactured by Canon Inc), OHP paper (Color BJ Transparency; CF 301 manufactured by Canon Inc) were set one after another with the press force kept contact to determine the voltage of the piezoelectric member S and as a result, it was found that the voltage value decreases in order of ordinary paper, glossy paper and OHP paper, i.e. ordinary paper>glossy paper>OHP paper. Thus, this can be used to discriminate the kind of paper.

Furthermore, in this Example, stainless steel (SUS 27) was used for the press member 12, but any material having a high Young's modulus, a high hardness and a wide elastic range may be used and for example, iron, nickel, chromium, tungsten and molybdenum are preferable, or alloys or oxides thereof, or aluminum oxides, silicon oxides, silicon nitrates and zircon oxides, or ceramics thereof, or glass or polymer materials may be used.

Furthermore, in this Example, phosphorous bronze was used for the flat spring 13 but instead thereof, for example, carbon steel, Si—Mn steel, Cr—V steel, brass and beryllium copper may be used. Furthermore, PZT (lead zirconate titanate) was used for the piezoelectric member S but instead thereof, for example, barium titanate, ZnO, and any material having a piezoelectric property may be used.

What is claimed is:

1. An apparatus for discriminating a kind of a sheet material, comprising:
    a substrate having a recessed portion;
    a press member situated so that a sheet material can be deflected using the recessed portion;
    a support member for supporting the press member such that the sheet material situated to cover the recessed portion is pressed by the press member;
    a sensor for detecting information corresponding to a deformation amount of the sheet material;
    means for discriminating a kind of the sheet material on basis of the information on the deformation amount of the sheet material detected by the sensor; and
    press member holding means for holding the press member,
    wherein the press member holding means holds the press member at a distance from the substrate when the sheet material is set in the substrate, moves the press member to a position near the recessed portion when the sheet material is pressed, and holds the press member so that the press member contacts the sheet material at a position other than the recessed portion, and
    wherein the press member holding means moves the press member along the sheet material, the sheet material is not deflected when the press member is located in a position other than the recessed portion, and the sheet material is deflected when the press member is located near the recessed portion.

2. The apparatus according to claim 1, wherein the sensor detects a deformation amount of the support member when the sheet material is not deflected and a deformation amount of the support member when the sheet material is deflected, and the kind of the sheet material is discriminated based on a difference therebetween.

3. The apparatus according to claim 2, further comprising:
    a second memory for storing a deformation amount of the support member when the sheet material is not deflected; and
    deformation amount difference calculating means for calculating a difference between a deformation amount of the support member when the sheet material is deflected and the deformation amount stored in the second memory.

4. The apparatus according to claim 3, further comprising:
    a third memory for storing as data a relationship between the difference in deformation amount and the kind of the sheet material; and
    a second discrimination unit for discriminating the kind of the sheet material from results by the deformation amount difference calculating means and data in the third memory.

5. The apparatus according to claim 1, wherein the sensor detects a change in deformation amount of the support member in a process of change in deflection amount of the sheet material, and the kind of the sheet material is discriminated based on the change in deflection amount.

6. The apparatus according to claim 5, further comprising:
    a fourth memory for storing as data a relationship between the change in deformation amount of the support member and the kind of the sheet material; and
    a third discrimination unit for discriminating the kind of the sheet material from the detected change in deformation amount of the support member and data in the fourth memory.

7. The apparatus according to claim 1, wherein the press member is a rotatably supported roller.

8. The apparatus according to claim 1, further comprising press force imparting means for imparting a press force to the press member.

9. The apparatus according to claim 8, wherein the press force imparting means tilts the press member holding means to apply a bending moment to the press member.

* * * * *